United States Patent
Hann et al.

(10) Patent No.: US 10,251,962 B2
(45) Date of Patent: Apr. 9, 2019

(54) SINGLE-PAIR EARPHONE STERILIZER WITH GERMICIDAL LIGHT

(71) Applicants: Robert Hann, Ridgewood, NY (US); Anthony John Serino, Harvard, MA (US)

(72) Inventors: Robert Hann, Ridgewood, NY (US); Anthony John Serino, Harvard, MA (US)

(73) Assignee: Robert Hann, Ridgewood, NY (US)

( * ) Notice: Subject to any disclaimer, the term of this patent is extended or adjusted under 35 U.S.C. 154(b) by 0 days.

(21) Appl. No.: 15/438,563

(22) Filed: Feb. 21, 2017

(65) Prior Publication Data
US 2017/0319725 A1 Nov. 9, 2017

Related U.S. Application Data

(60) Provisional application No. 62/297,384, filed on Feb. 19, 2016.

(51) Int. Cl.
*A61L 2/10* (2006.01)
*H04R 1/12* (2006.01)
*H04R 1/10* (2006.01)

(52) U.S. Cl.
CPC ............ *A61L 2/10* (2013.01); *H04R 1/12* (2013.01); *A61L 2202/10* (2013.01); *H04R 1/1091* (2013.01); *H04R 2460/17* (2013.01)

(58) Field of Classification Search
CPC .. A61L 2/10; A61L 2202/10; A61L 2202/122; A61L 2202/123; A61L 2202/16; A61L 2202/24
See application file for complete search history.

(56) References Cited

U.S. PATENT DOCUMENTS

| | | | | |
|---|---|---|---|---|
| 3,776,694 A * | 12/1973 | Leittl | ............ | A61L 2/10 312/206 |
| 6,096,264 A * | 8/2000 | Peifer | ............ | H02J 7/0027 206/351 |
| 7,225,559 B1 * | 6/2007 | Padilla | ............ | F26B 9/003 34/202 |
| 2012/0176241 A1 * | 7/2012 | Pasch | ............ | A61L 2/10 340/540 |
| 2014/0056758 A1 * | 2/2014 | Trabalka | ............ | A61L 2/10 422/24 |

* cited by examiner

*Primary Examiner* — Timothy C Cleveland
(74) *Attorney, Agent, or Firm* — Buchalter, a professional corp; Kari Lynn Barnes

(57) ABSTRACT

Apparatus and methods include a single-pair earphone sterilize with germicidal light. Embodiments include a housing and a germicidal light source. The apparatus may include circuitry, such as power, to support the germicidal light source and a divider to shield the circuitry from the germicidal light source. The apparatus may also include attachment portions to position and maintain earphones in a position relative to the germicidal light source.

11 Claims, 11 Drawing Sheets

SINGLE-PAIR EARPHONE STERILIZER WITH GERMICIDAL LIGHT

BACKGROUND

Earphones are often stored in unsanitized places such as pockets, pocketbooks, backpacks, and car dashboards. They are therefore likely to come in contact with bacteria and microorganisms that may present unhealthy effects when inserted into the ear.

SUMMARY

With the growing popularity of personal and portable audio playback devices, such as, for example, portable phones and computer equipment, there is a corresponding rise in the use of personal earphones that make direct contact with the ear. Audio playback devices are also found in a number of travel locations that require use of personal earphones, such as schools for computers, videos within automobiles, and entertainment systems within airplanes. Often these earphones are stored in potentially unhygienic places which may introduce contamination to the earphones, thereby increasing the prospect of bacterial contamination to the ear. Exemplary embodiments described herein include a low cost apparatus that disinfects different types of earphones using a germicidal light source to reduce the proliferation of bacteria on the earphones.

Exemplary embodiments include an apparatus configured to sterilize a variety of earphones, including in different shapes, sizes, and models, in a quick and efficient fashion. Efficient is considered in terms of the ability of the user, so that it is easy enough that a layperson with no experience in electronics or sterilization could use it with desired results.

An exemplary embodiment includes methods and apparatuses for sterilizing earphones using an external germicidal light source that is separate from or not embedded in the earphones or any component of the earphones themselves.

Exemplary embodiments of the sterilizing light may include a small light source of ultraviolet (UV) radiation and powered via an onboard power source, such as disposable batteries, rechargeable batteries, plug, and combinations thereof. A circuit board, and software stored and executed by a processor mounted on the circuit board, may control the length of time that the sterilizing light is illuminated as well as any other general on/off and voltage regulation needs. In an exemplary configuration, the sterilizing light may be mounted in such a fashion as to be exposed to a portion of an interior cavity, such as for example, positioned within the top half of the box, while shielding another portion of the interior cavity, such as within the lower half of the box. In this case, the shielded portion of the box may contain the power source and circuit board; thereby protecting and concealing these components from the UV radiation. When engaged, the sterilizing light preferably disrupts, kills, or inactivates microorganisms by means of short-wavelength light radiation.

In an exemplary embodiment, the user may open the box, place earphones inside, close the lid, activate the box by switch or automatically upon closing the box, and wait for the cleaning to take place. The system may automatically stop after a given time. Finally, the user can open the box and remove the earphones, which are now sterilized at the point of contact with the ear, and are ready for use.

FIGURES

FIGS. 1-3 illustrate an exemplary embodiment in which FIG. 1 represents a front side elevation view of an exemplary embodiment in a closed position, FIG. 2 represents a lateral side elevation view of an exemplary embodiment in an open position, and FIG. 3 represents a top elevation view of an exemplary embodiment with an upper portion, or lid section removed.

FIGS. 4-6 illustrate an exemplary embodiment in which FIG. 4 represents a front side elevation view of an exemplary embodiment in a closed position, FIG. 5 represents a lateral side elevation view of an exemplary embodiment in an open position, and FIG. 6 represents a top elevation view of an exemplary embodiment with an upper portion, or lid section removed.

Figure 7:
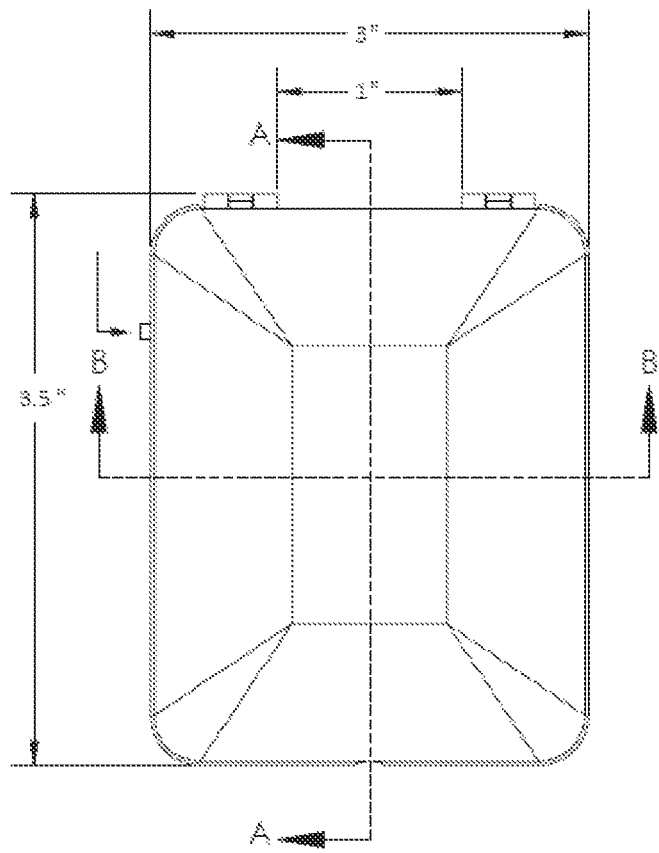
Figure 8:
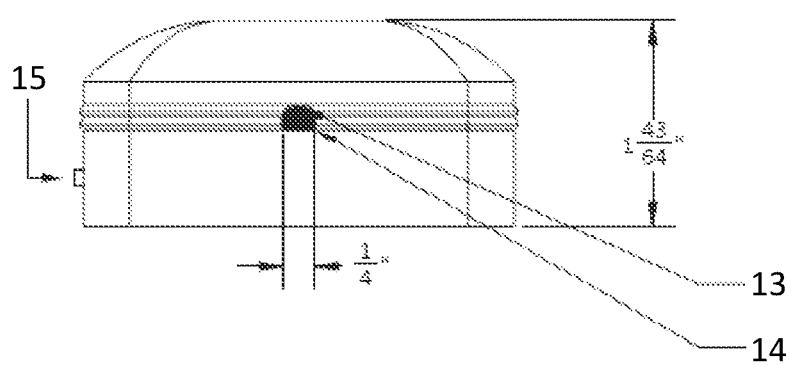
Figure 9:
Figure 10:
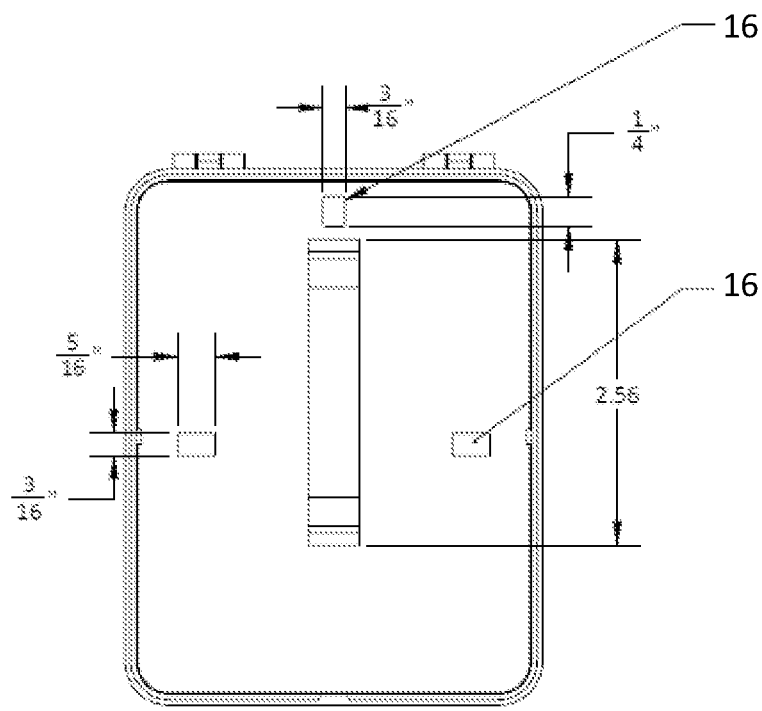
Figure 11:
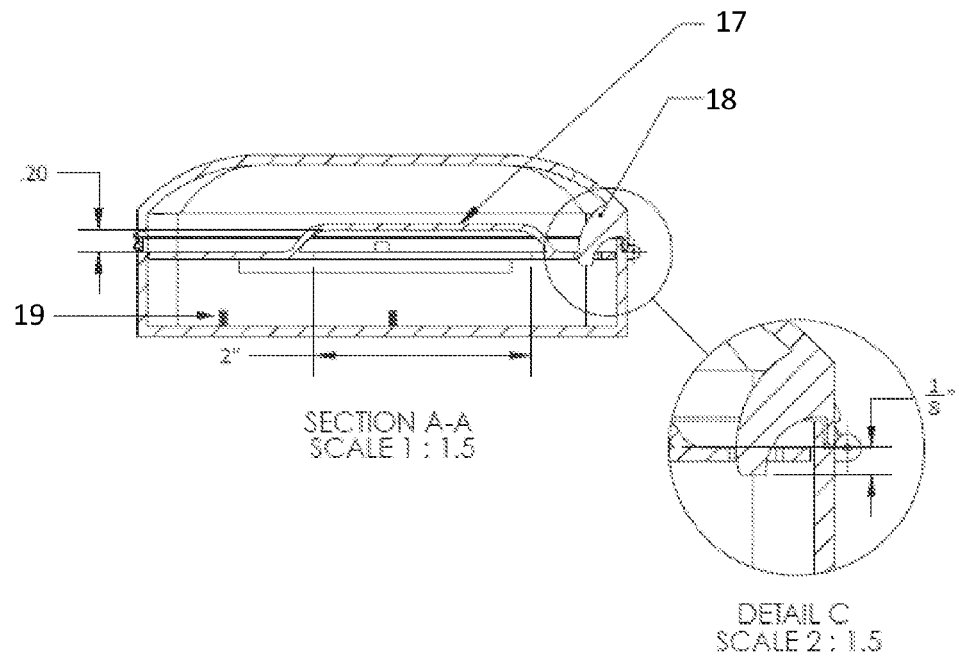
Figure 12:
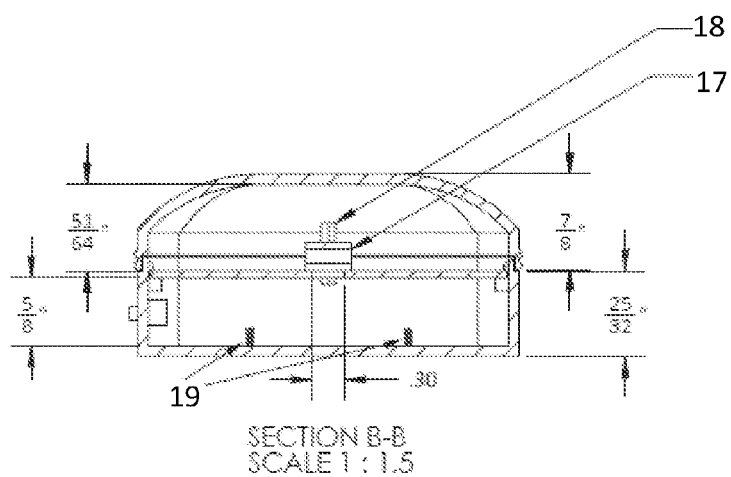

FIGS. 7-12 illustrates an exemplary embodiment drawn to scale to illustrate exemplary dimensions for an earbud application. Illustrated dimensions are shown in inches. FIG. 7 is a top elevation view; FIG. 8 is a front side elevation view; FIG. 9 is a lateral side elevation view; FIG. 9 is a top elevation view with the lip portion of the housing removed; FIG. 11 is a cut away view along section A-A of FIG. 7; and FIG. 12 is a cut away view along section B-B of FIG. 7.

Figure 13:
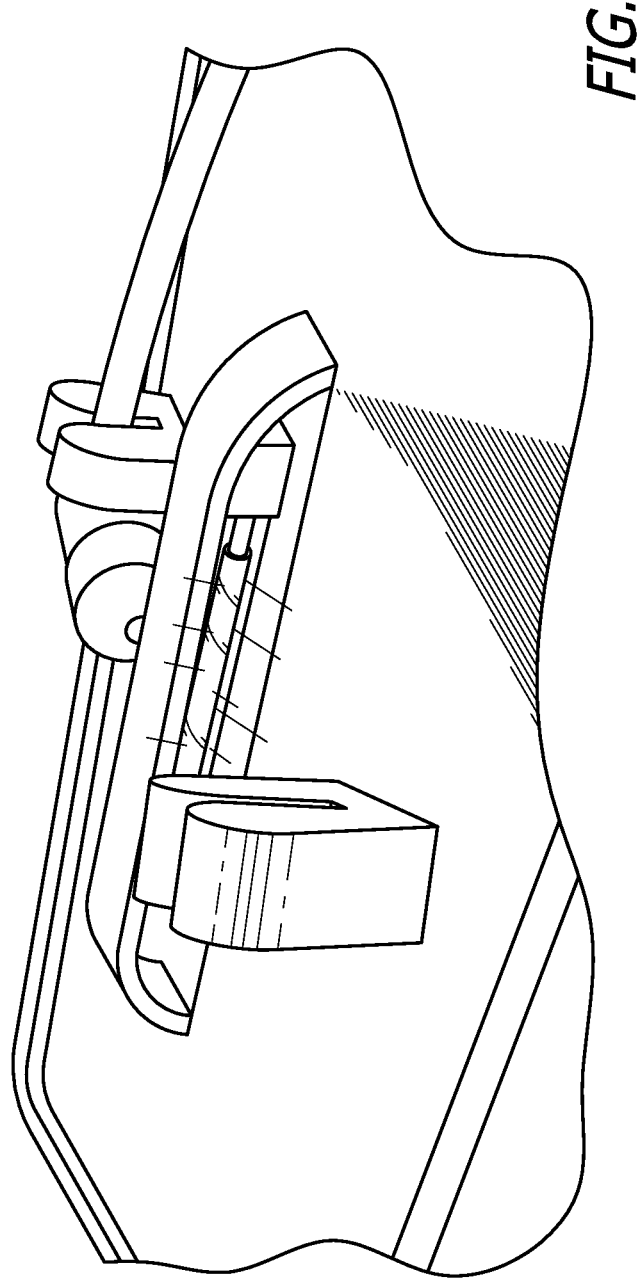
Figure 14:
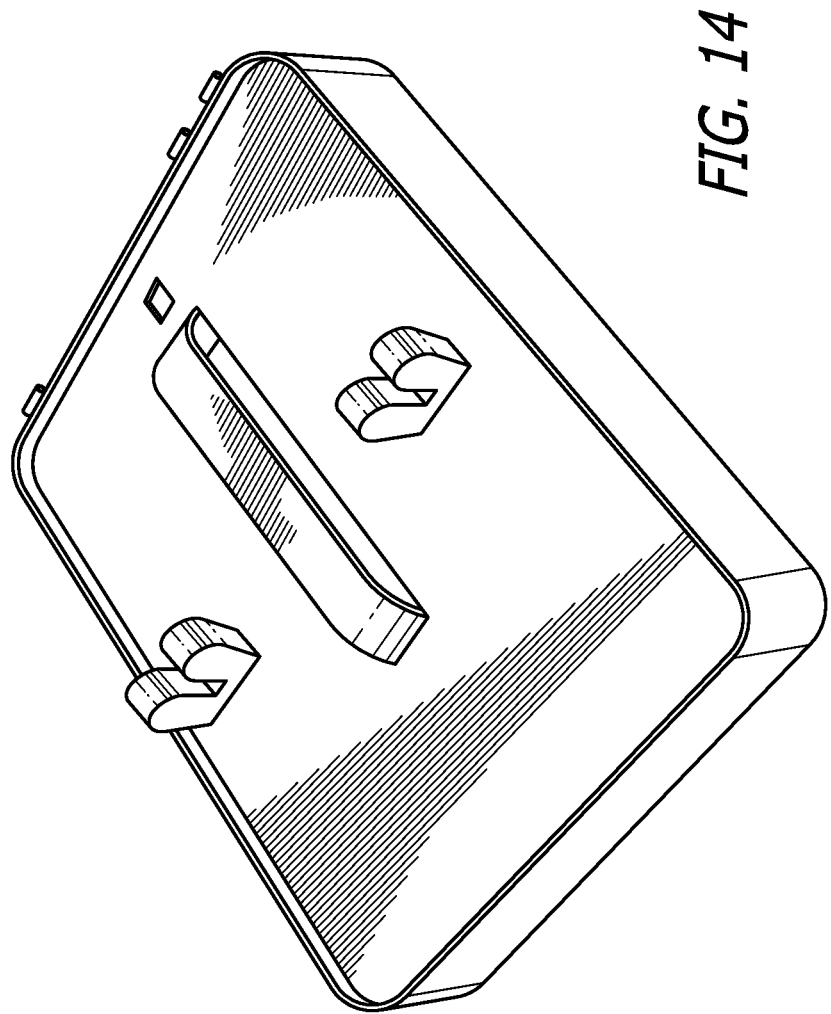
Figure 15:
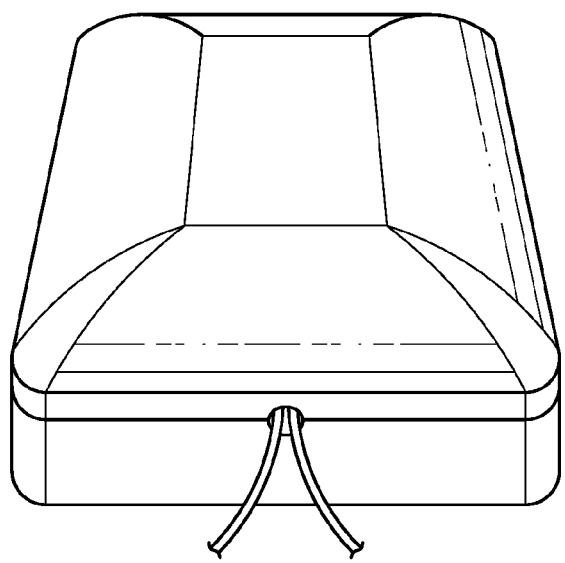

FIGS. 13-15 illustrate additional features that may be used in combinations described herein. FIGS. 13-14 illustrate an interior portion of the housing with the lid portion removed from different perspective viewpoints. FIG. 15 illustrates an exemplary housing in a closed configuration with the access aperture for the earphone cord extending through the housing wall.

Figure 16:
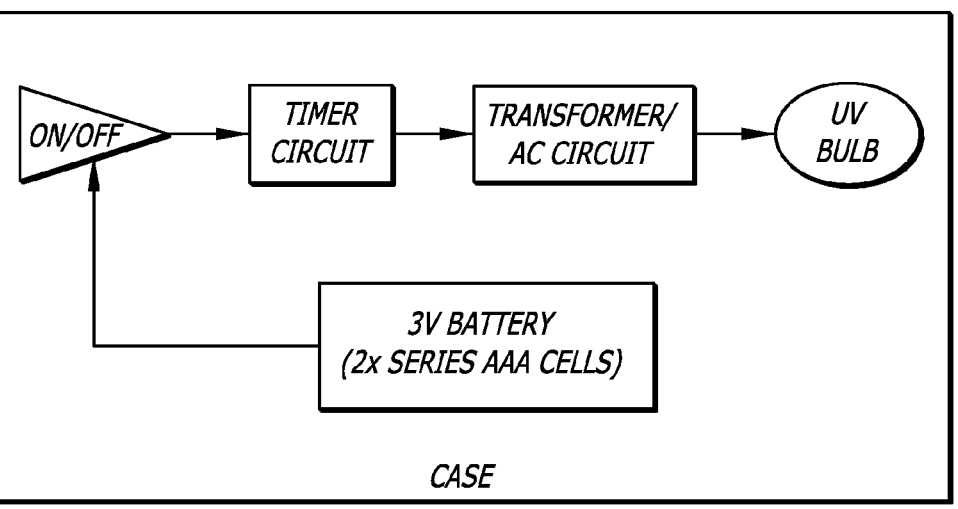
Figure 17:
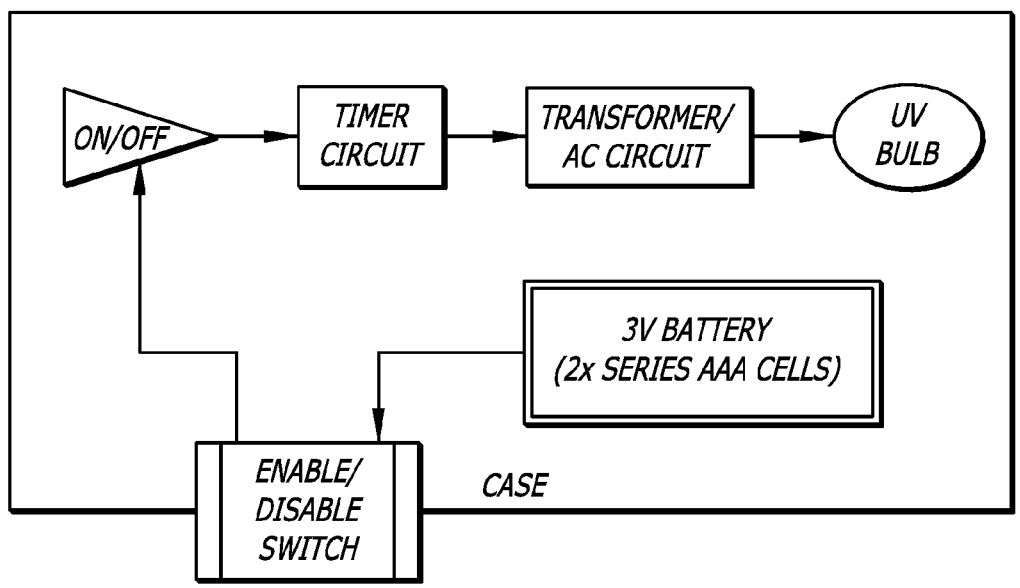
Figure 18:
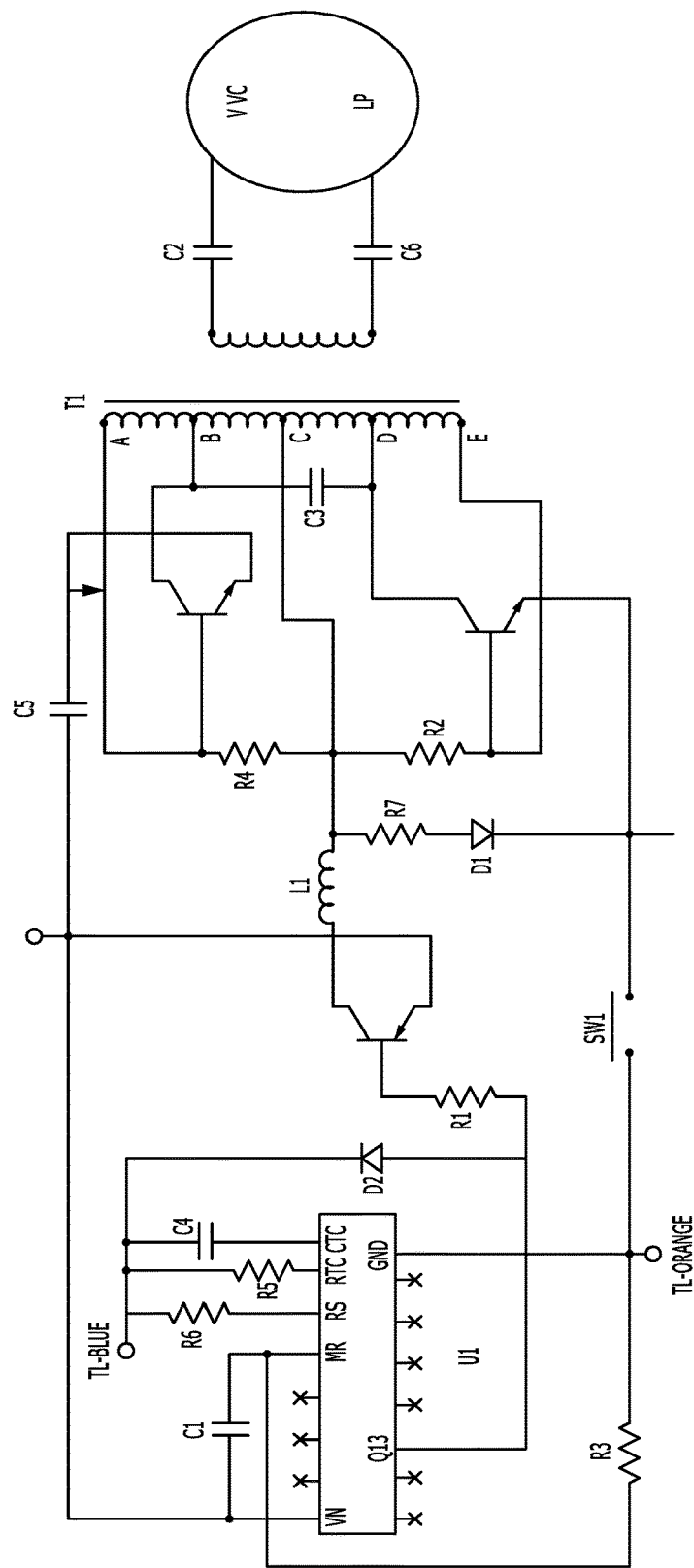

FIGS. 16-18 illustrate exemplary embodiments of component circuitry to achieve the functions described herein.

DETAILED DESCRIPTION

The following detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. It should be understood that the drawings are diagrammatic and schematic representations of exemplary embodiments of the invention, and are not limiting of the present invention nor are they necessarily drawn to scale. However, the figures may support the written description and claims, such as in some cases, for the relative sizes and/or relative positions of components or objects.

Exemplary embodiments described herein relate to methods and apparatuses for sterilizing electronic and/or acoustic earphones, headphones, headsets, and earbuds (referred to collectively as earphones) using a germicidal light source. Although the exemplary embodiments are described in terms of ultra-violet radiation, the invention is not so limited. Exemplary embodiments of germicidal light may include short wavelength light that inhibits growth, inhibits reproduction, kills, or otherwise interferes with the proliferation of a germ, such as a bacteria.

Figure 1:
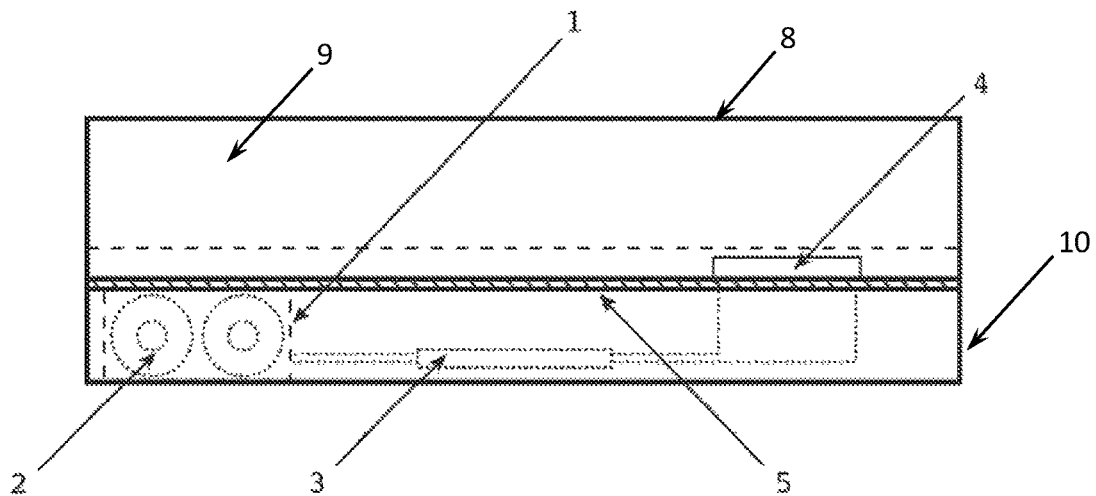
Figure 2:
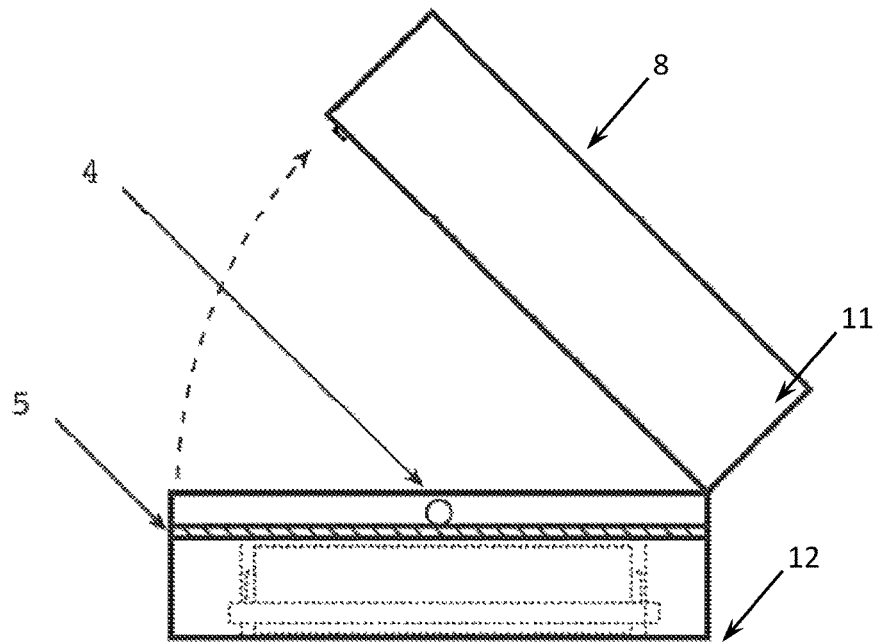
Figure 3:
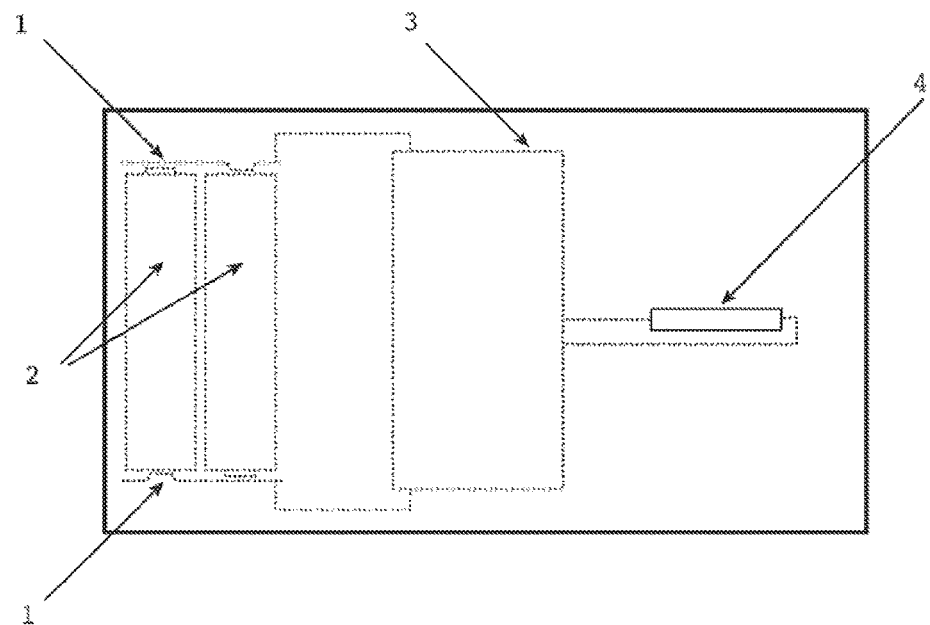

FIGS. 1-3 illustrate an exemplary embodiment in which FIG. 1 represents a front side elevation view of an exemplary embodiment in a closed position, FIG. 2 represents a lateral side elevation view of an exemplary embodiment in an open position, and FIG. 3 represents a top elevation view of an exemplary embodiment with an upper portion, or lid section removed. Exemplary components may be enclosed within a housing. As illustrated, enclosed components are represented by dotted lines to indicate a relative position, but represent that the component parts may not be directly visible to a user.

FIGS. 1-3 illustrate an exemplary apparatus having a housing 8, germicidal light source 4, circuit board 3, and power supply 2. In an exemplary embodiment, the light source 4 is positioned such that, when on, the germicidal light source 4 illuminates a first portion of a cavity defined by the housing 8. The housing 8 may include a barrier 5 that segregates the first portion of the cavity from a second portion 10 of the cavity. The first portion 9, second portion 10, and light source 4 may be configured to prevent or reduce light from the light source 4 from entering the second cavity. In an exemplary embodiment, the first portion 9, second portion 10, and light source 4 may be configured or positioned to reduce or prevent harmful radiation (such as ultraviolet radiation) from hitting components enclosed in the second portion. The second portion 10 may enclose electronic componentry, such as, for example, power supply 2, circuit board 3, and connections therebetween. The housing may include additional support structures, or sections, such as battery housing 1 to support and retain the component parts in their respective positions in the housing.

As shown, the power supply 2 may comprise batteries, which are connected from their associated terminals by electric wires to the circuit board 3, which connects to the light source 4 by electric wires. As best illustrated in FIG. 1, the light source 4 may be elevated above the divider 5 and project into the first portion of the cavity. The first portion may be defined by an upper portion (such as a lid portion) of the housing 8 including a top and lateral sides. In the closed position, the first portion of the cavity may be fully enclosed by the upper portion of the housing and the divider 5. In the open position, the first portion may be exposed to the outside and accessible for removably positioning earphones therein, and a gap or opening formed between the lateral sides of the upper portion of the housing and the divider.

FIG. 1 illustrating a front view of the apparatus illustrates an exemplary configuration in which the batteries 2, circuit board 3, and corresponding electronic componentry (collectively referred to as the supporting electronic components) lay beneath a protecting divider 5. As shown, the batteries 2, circuit board 3, and connecting electronic components complete an electric loop with the light source 4, which is protruding upwards from the divider 5 on an opposing face from that in which the supporting electronic components are positioned. The second portion may be defined by a lower portion (such as a base portion) of the housing 8 including a bottom and lateral sides. The second portion may be an enclosed cavity by the lower portion of the housing and the divider. Therefore, in an exemplary embodiment, opposing sides of the divider may define portions of the first and second portions of the cavity, respectively.

As seen in FIG. 2, the housing 8 may comprise a first portion 11 and a second portion 12. The housing may be repositioned from an open configuration providing access to an interior cavity of the housing and a closed configuration in which the housing fully encloses the light source such that light from the light source does not exit the enclosure of the housing. In an exemplary embodiment, the first portion 11 may be attached to the second portion 12. The first portion may rotate relative to the section portion, such as at a hinge positioned along an edge between the first portion and second portion. The first portion may define a top and lateral sides around a perimeter of the top, while the second portion may define a bottom and lateral sides around a perimeter of the bottom. The lateral sides of the first portion and second portion may be configured to mate. Mated surface may be by an edge that approximates the same shape and side in cross section, by an indentation/projection, by a lip or overhang, or some other configuration. In an exemplary embodiment, the mated surfaces limit the amount of light that escapes from between the first portion and second portion when in a closed configuration.

As used herein "fully encloses" and "does not exit" are used to approximate the configuration in which no light escapes the housing in a closed configuration. However, given the non-dimensional size of photons, it may be that a small amount of extraneous light does escape through the separation of individual components, and/or through access apertures as described herein. Even though a small percentage of light may escape, a housing may still define a fully enclosed light source such that the light does not exit the enclosure. A person of skill in the art would appreciate what constitutes a fully enclosed housing, while still allowing for minute leakage based on the objectives and functions of the component parts and arrangements as described herein.

Exemplary embodiments described herein include an elongate light source 4. As seen in FIG. 3, the light source may be positioned generally central or midway across a first dimension of the housing. The elongate light source may define a longitudinal axis that is generally perpendicular to the first dimension. The elongate light source is configured to illuminate at least a first side of an earphone positioned adjacent the light source. The light source is positioned and configured to at least a portion of light radially outward and in opposing directions from the light source. For example, the light source may project light on opposing sides of the light source as seen from the above perspective, as illustrated in FIG. 3. In this way, one side of the earphones may be positioned on opposing sides of the light and direct light at the contact portion of the earphones to the ear.

Figure 4:
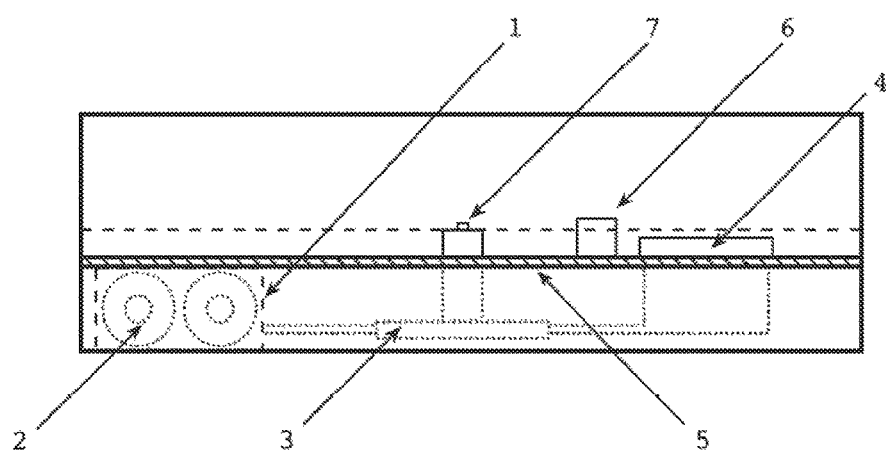
Figure 5:
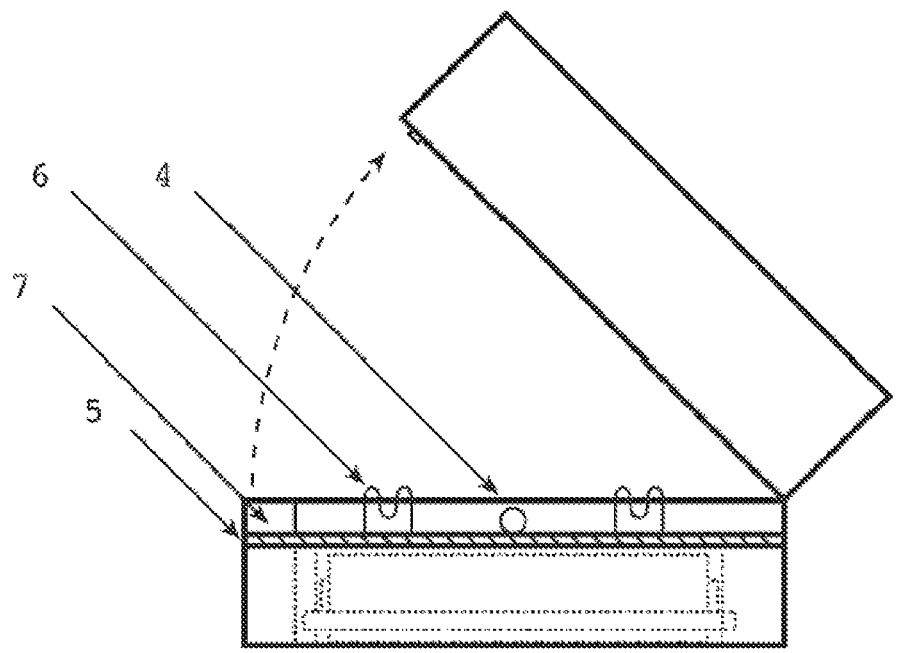
Figure 6:
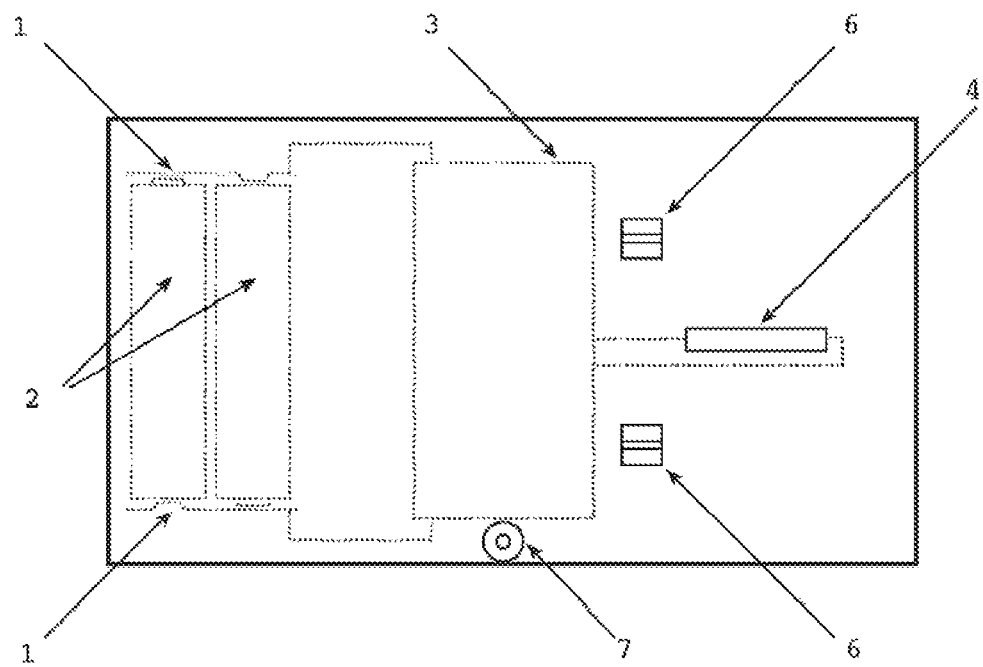

FIGS. 4-6 illustrate an exemplary embodiment in which FIG. 4 represents a front side elevation view of an exemplary embodiment in a closed position, FIG. 5 represents a lateral side elevation view of an exemplary embodiment in an open position, and FIG. 6 represents a top elevation view of an exemplary embodiment with an upper portion, or lid section removed. Exemplary components may be enclosed within a housing. As illustrated, enclosed components are represented by dotted lines to indicate a relative position, but represent that the component parts may not be directly visible to a user.

FIGS. 4-6 illustrate an exemplary apparatus having a housing 8, germicidal light source 4, circuit board 3, and power supply 2. In addition to similar component parts as described with respect to FIGS. 1-3, the present embodiment may include additional features.

In an exemplary embodiment, the apparatus may include a switch 7 that activates the light source 4. The switch may be on an exterior surface of the housing 8, such that a user may manually activate the light. The switch may be within the enclosure of the housing, and/or coupled to the housing to detect when the housing is in a closed or open configuration to automatically activate the light. As illustrated, the switch may include a push button that is engaged by the upper portion of the housing in a closed positioned and disengaged when the housing is in an open position. The switch may couple to the circuit board and open and/or close the circuit loop to activate the light when the housing is in the closed configuration.

As seen in the profile view of FIG. 5, the switch may be a button that is positioned along a perimeter of the box opposite the hinged side of the two portion housing. The first portion of the housing may include a projection that depresses the switch in the closed position, and/or may latch the first portion to the second portion. The switch may also extend upwardly past the lower portion of the housing, such that the upper portion of the housing may directly engage the switch. The first portion may also mate with a lipped or flanged portion of the second portion, in which case the button may be engaged by the projecting portion of the lip or flange. The relative positions of the switch and engagement component may be switched from the first portion of the housing to the second portion of the housing. However, as illustrated, the passive (or non-electrical component being the engagement component) portion is positioned on the first portion of the housing away from the electronics and power source, permitting the active component (the switch) to be positioned adjacent the power supply and internal supporting electronics.

In an exemplary embodiment, the apparatus may include attachment portions for securing the earphones to the apparatus in a desired configuration or position relative to the light source. One or more attachment portions 6 may be included to accommodate different earphone configurations. For example, attachment portions 6 may include indentation, detent, clip, hook and loop fasteners, cradle, hook, strap, buckle, snap, and any combination thereof. The one or more attachment portions may be positioned in the housing relative to the light source to properly position the attached earphone in the desired position relative to the light source. For example, a first set of attachment portions 6 may be positioned adjacent the light source on lateral sides of the elongated light to accommodate earbud type earphones, while a single section attachment portion may be positioned adjacent a longitudinal end of the elongate light source to secure an over the head (headband) portion of a unitary headphone arrangement. Different attachment portions may be used to accommodate different earphone configurations. For example, clips may be used to secure various size earbuds, while a strap having hook and loop connectors may be used to secure an over the head headband type headphone.

In an exemplary embodiment illustrated in FIG. 6, two earphone mounts 6 are fixed to the divider 5 in order to keep the earphones in place while the light source is on. Also visible is the automatic power-on switch 7, which is engaged when the box is closed, thereby turning on the light source. FIG. 5 shows a side view of the apparatus with the lid open. Since the automatic power-on switch 7 is not depressed, the light source will not be activated.

FIGS. 7-12 illustrates an exemplary embodiment drawn to scale to illustrate exemplary dimensions for an earbud application. Illustrated dimensions are shown in inches. FIG. 7 is a top elevation view; FIG. 8 is a front side elevation view; FIG. 9 is a lateral side elevation view; FIG. 10 is a top elevation view with the top portion of the housing removed; FIG. 11 is a cut away view along section A-A of FIG. 7; and FIG. 12 is a cut away view along section B-B of FIG. 7.

FIGS. 13-15 illustrate additional features that may be used in combinations described herein. FIGS. 13-14 illustrate an interior portion of the housing with the lid portion removed from different perspective viewpoints. FIG. 15 illustrates an exemplary housing in a closed configuration with the access aperture for the earphone cord extending through the housing wall.

In this embodiment, the first portion of the housing is shaped or contoured to improved aesthetics and reduce overall volume of the housing. This exemplary embodiment also includes additional features as described herein.

In an exemplary embodiment, the housing may include an aperture for accommodating a cord of the earphones. Given the potential effect on plastics and other component parts, the housing may be configured to enclose just the portion in contact with or adjacent to the portion that is in contact with a user. Therefore, the remainder of the cord may be positioned outside of the housing. As shown in FIG. 8, the housing may include an aperture 13 for accommodating a cord therethrough when the housing is in a closed position. The aperture 13 may be defined by an indentation in the lid portion of the housing that does not contact the base portion of the housing when in a closed position. Therefore, a perimeter of the aperture is defined by both the lid and base portions of the housing. In an exemplary embodiment, a stopper 14 may be included adjacent or approximate a portion of the aperture to minimize light leakage when in use. For example, a portion or all of the aperture perimeter may be line by a flexible material to create a perimeter similar to a gasket. The flexible material may be configured to contact the passed cord and deflect to varying degrees based on the thickness of the passed cord. Therefore, the flexible material may contact a substantial amount of the cord and minimize light escaping through the aperture. Other stopper configurations may be used, such as a flap, lining, curtain, non-linear aperture path, etc. in order to minimize light output.

In an exemplary embodiment, a cord winder may be included. Other cord storage components may alternatively be used, such as a pronged support, enclosure, etc. The winder may be automatic or manual. The winder may rotate to wind the earphone cord or may be static such that the cord is wound around a stationary component. The cord holder may be on an exterior or interior surface of the housing. The cord winder may be on an exterior surface of the housing. In this case, the cord aperture may be used such that, when the earbuds are in a cleaning position within the housing, the cord may traverse the housing wall and be stored adjacent an exterior surface of the housing. In an exemplary embodiment the cord holder may be on an interior of the housing. In this case, the cord may be compartmentally separated from the germicidal light source.

In an exemplary embodiment, the housing may also support a manual switch as described above. The manual switch 15 may be positioned on an exterior of the housing for illuminating the interior when in a closed configuration. The switch 15 may permit a user to turn the apparatus on and off. The switch 15 may be used in conjunction with, in place of, or in any combination with an automatic switch described herein. For example, the apparatus may include one or two switches for a combination of automatic and manual control. In an exemplary embodiment, a three position switch may be used to turn the apparatus on, off, or configure the device into an automatic mode, while a second switch, such as the button switch described above, detects and controls the light source in the automatic configuration.

In an exemplary embodiment, the interior portion may be further subdivided or segregated, similar to the inclusion of barrier 5, such that the housing may enclose the entire earphones, but a cavity is defined within the housing that encloses the light source. In this case, the cord may pass through a second barrier such that the first portion of the enclosure is subdivided into a light source portion and a protected portion. The apparatus may be configured to store a substantial portion of the cord or other portion of the earphones, while the light source portion is configured to enclose the light source and the portion of the earphones to be sterilized, such as the earbuds.

In an exemplary embodiment, the light source has an elongate dimension larger than the length of a portion of the earphones in contact with the inner portion of the ear. The elongate light source as illustrated comprises a single light source configured to emit light along a longitudinal length of the light source. An elongate light source may also be defined by a plurality of point light sources or non-elongate light sources positioned along a longitudinal length to approximately the effect from a single light source. In either case, the one or more light sources define a longitudinal length in which the emitted light has a vector component propagating radially away from the longitudinal axis.

As shown in FIG. 10, one or more holes 16 may be positioned on divider 5 to accommodate various components traversing across barrier 5. For example, a first set of holes 16 may be used to support earphone holders, while one or more holes 16 may be used to accommodate the switch and/or latch.

As seen in FIG. 11, the apparatus may also include a shield 17 positioned over the elongate light source. The shield 17 may block light emitted by the light source from being directed toward a user, if the light is engaged when the housing is in an open position. As shown, the shield is a generally planar, elongate component coupled to the divider 5 at opposing ends adjacent the longitudinal terminal ends of the elongate light source. The shield thereby defines an opening between the shield and the divider for directing light in planar opposing directions from the light source, generally parallel to the divider or bottom of the housing. The shield may have a length longer than the elongate light source. The shield may also or alternatively protect the light source from direct exposure or contact to reduce the likelihood of it being broken or damaged during use.

As seen in FIG. 11, an exemplary automatic actuator 18 is illustrated, configured to engage a switch and turn the light source on when the housing is in a closed configuration. As illustrated, the actuator is configured to depress a button switch on an opposite side of the divider than the lid portion of the housing, or from the illumination side of the cavity. In this way, a user may be limited from activating the device when the housing is not closed. For example, the actuator may include a projection permanently attached to a lid portion of the housing that is configured to pass through an aperture in the divider and enter a space on the opposing side of the divider from the lid portion. The actuator may be positioned such that it contacts and depresses a switch when the lid is in a closed position or otherwise mated with the base portion of the housing. The projection may be sized such that it would be difficult for a user to depress the switch without the projection. In an exemplary embodiment, the projection may be within the aperture in a closed and open position, preventing access to the switch by a user.

As seen in FIG. 12, posts or other connectors 19 may be used to support the internal componentry and retain relative positions relative to the base portion of the housing. For example, circuit board, batteries, or other electronics may be supported by posts to separate the circuit board from the housing.

FIG. 13 is an exemplary close-up of the internal compartment of the housing, for example, with the housing lid removed, and one earbud in a configuration to be cleaned. As shown, exemplary attachment portion 6 may be a clip that accommodates various sized earbuds. The clip may include faced projections configured to deflect when an earbud is positioned therebetween and clamp the earbud into a desired configuration. The clip may comprise a compressible material such that a frictional engagement is created by the compression of the clamp material by the earbud. The clip may also comprise arms that move relative to each other such that they move away from each other when the earbud is positioned therebetween, but have a biased closed position such that they impose pressure on the earbud when positioned therein.

In an exemplary embodiment, the attachment portions are rotatable with the application of sufficient pressure, such that a user can position the attachment portion in a desired configuration, but such that the attachment portion maintains the desired configuration when in a closed position. In this way, a user may target a specific portion of the earphone during cleaning. For example, as shown the illustrated earbuds comprise an opening and a lipped portion that defines a cavity with an internal dimension greater than the opening. Therefore, the projected light may not contact an entire interior of the earbud. A user may therefore rotate the attachment portion such that the opening of the earbud is angled with respect to a radial axis of the light source. The user may position the earbud such that the earbud opening generally faces toward the light source, where the light enters the opening and generally strikes a first side of the earbud. The user may then close the housing and clean the earbud for a period of time. The user may then reposition the attachment portion such that the opening is still generally toward the light source, but where the light enters the opening and generally strikes a second side of the earbud thus cleaning a different portion of the earbud.

FIGS. 16-18 illustrate exemplary embodiments of component circuitry to achieve the functions described herein. For example, FIG. 16 includes a power supply, switch, timer circuit, and light source, and components to convert the current from the power source usable for the light source. In this case, the switch may be an automatic or manual switch according to embodiments described herein. The timer circuit may be used with either switch configuration to illuminate the enclosed earphones for a period of time. The time circuit may be used to turn off the light source after a period of time to reduce the wear imposed on the earphones by use of the sterilizing light. FIG. 17 is similar to FIG. 16, but includes the two switch configuration, in which a user may have a manual override to disengage the light source. In this way, the housing may be used simply as a carrying case, and not a cleaner device. FIG. 18 illustrates a full circuit diagram illustrating exemplary componentry.

Exemplary embodiments are shown and described herein. These embodiments are not intended to be limiting but show exemplary features, components, and configurations. These features, components, and configurations may be duplicated, deleted, sub-divided, combined or otherwise reconfigured and stay within the scope of the present disclosure. Components or features may also include equivalent features or components as would be understood by a person of skill in the art. For example, equivalent light sources, power sources, containers, etc. may be exchanged for those disclosed herein.

Specific examples of alternative arrangements are now specifically described for illustration only and are not intended to be limiting.

First Exemplary Embodiment

In an exemplary embodiment, all relevant equipment for the apparatus is housed inside a box that will be lightweight and portable. The inside of the box will contain a power source, a circuit board, a divider that protects and conceals these parts, and a sterilizing light source. The outside of the box will have the product's name and any other relevant data necessary to protect the invention such as "patent pending" information, manufacturing location, etc.

Second Exemplary Embodiment

In an exemplary embodiment, the box will have both top and bottom sections that will open and close by use of a hinge or hinges. There will be clips, mounts, or other attachment mechanisms that secure the earphones in place so that the area of the earphones that come in contact with the user's ears will face towards the sterilizing light. An automatic power-on system will be incorporated via a simple switch that engages the sterilizing light when the lid is closed. When the box is closed, a simple locking mechanism (such as a malleable plastic clasp) will securely fasten the top and bottom sections together. The sterilizing light source will be ultraviolet light, which will be illuminated for less than 10 minutes. The box will be made from plastic, which will be manufactured as primarily opaque, but it will also have sections of transparent plastic so that the user can see when the light is turned on. The unit will use the minimum power required, such as AAA batteries.

Third Exemplary Embodiment

In an exemplary embodiment, the box will contain a plastic button-plunging arm that will depress a button which completes an electric circuit and activates the germicidal light when the lid of the box is closed. In this way, the germicidal light cannot be lit while the box is open. To aid in opening the box, the exterior of the box will have textured plastic lines along the top which will provide a grip for the user to flip open the top of the box while holding the bottom of the box in their other hand. The box will have a small half-hole ("mousehole") that allows the cord of the earphones to come out of the box without disrupting the integrity of the box's seal.

Inside the box there will be a thin plastic "deck" piece that conceals the battery and electronics which are housed beneath the deck in the bottom half of the box. The deck is a removable drop-in tray that sits on two ledges which protrude from the interior walls, and it stays in place with two small nubs on the interior walls above the tray. The deck will have one small square cut out (3/16" wide by 1/4" long) to allow the plastic button-plunging arm to pass through as it goes to depress the button when the top is closed. The deck will have a long rectangular hole (2.56" long by 0.30" wide) that is slightly longer than the germicidal light bulb so that the light bulb can protrude above the deck; this allows the germicidal light source to shine directly on to and within close proximity to the earphones. Above the long rectangular hole in the deck is a plastic bridge which protects the germicidal light source from accidental breakage. The deck will have two small rectangular cut outs (5/16" wide by 3/16" long) that fit (or hold) the two clips that keep the earphones in place for maximum sterilization from the germicidal light source. The clips will be shaped like the letter "Y", with the upper projections generally curved to create a goblet-like cross section. The clips will be made from a soft, malleable plastic that allows for the placing in and removal of earphones of various sizes. The clips can be installed into the deck by inserting them through the small, rectangular cut outs and turning them 90 degrees.

The dimensions of the box will be 4 21/32 inches long by 3 9/26 inches wide by 1 43/64 inches tall. The germicidal light source will be a low pressure microbial disinfecting mercury-arc ultraviolet lamp which operates at a wavelength between 200-280 nm (UV-C) with a spectral peak of 253.7 nm using 9-watts of power. The light will be programmed to illuminate for five minutes, then it will automatically shut off until the user opens the lid and closes it again. Using this type of a low infrared radiation light source for five minutes will sterilize the components that come in direct contact with the ear, while protecting the integrity of the earphones themselves.

Use Flow 1

In an exemplary embodiment, a method is provided in which earphones by be cleaned. In an exemplary embodiment, a user may open a lid of the housing, position the earphones in the box, close the lid. The germicidal light thereafter, once the lid is closed, illuminates for a specified time. A user then opens the lid and removes the earphones for next use.

Fourth Exemplary Embodiment

In an exemplary embodiment, the batteries will be rechargeable with an external cord which is plugged into the box and recharges the batteries via a standard home wall-plug or common USB port. A switch will be attached to the outside of the box which allows the user to activate the germicidal light source, while an electronic timer will determine when the germicidal light source will be automatically turned off. Alternatively, the user can decide to manually turn off the germicidal light source by turning the switch to the off position, which cuts the supply of power to the circuitry. Even with an on/off switch, the box lid will still have a plastic button-plunging arm that will depress a button to ensure that the germicidal light cannot be lit while the box is open. The box will have a small hole that allows the cabling of the earphones to come out of the box and the hole will be surrounded with a rubber gasket (or grommet) to allow the wires to come out of the box without letting germicidal light escape the box while the circuitry is on. When wireless earphones are to be cleaned, and no wire is present, the rubber gasket will seal the hole entirely. The interior of the bottom section of the box will have plastic raised substrate (female) screw posts to allow the circuitry and power supply to be mounted to the box via small thread metal screws. The dimensions of the box will be 3.5" long by 3" wide by 1.6" tall.

For this exemplary embodiment, a user may clean earphones by opening the lid, placing the earphones in the box, positioning the cabling through the opening; closing the lid; and manually engaging the switch. The germicidal light illuminates for a specified time while the lid is closed. A user then opens the lid and removes the earphones.

Alternative Exemplary Features

Other germicidal light sources could be used instead of ultraviolet. In an exemplary embodiment, incandescent UV light is used. When engaged or activated, the sterilizing light may disrupt, kill, or inactivate all or substantially all (for example, more than 80-90%, 90-100%, or any percentage within the exemplary ranges) of the microorganisms by means of light-sourced radiation.

Exemplary light sources may be located in an upper portion of a container, that includes a divisor or other separator to keep the electronics and other internal components protected from the contaminants of the earphones and/or exposure and potential deterioration from the light source. The light source may be positioned with respect to the mounting forms such that a substantial portion of the light is directed onto the skin contacting surfaces of the ear buds. One or more light sources may be used. For example, light sources may be integrated or attached to the container lid, walls, or divider wall to provide coverage over one or more surfaces of the earphones.

The length of time that the light is illuminated could be altered. For example, the sterilizing period may be for 1-10 minutes, 2-5 minutes, or other desired sterilization time that may be programmed into the box. The sterilization period may be programmable such that a user can choose a desired sterilization time. Alternatively, the sterilization time is pre-programmed such that the box sterilizes for the same amount of time whenever closed and activated.

Other mounting forms or earphone securement mechanisms may be used. For example, clips, snaps, claws, hoops, hooks, etc. may be used to secure and orient the earbuds of the earphones toward the light source.

The box could contain a wire-winding device to minimize the chances of the earphone wires becoming tangled. The box could have an open end so that the earphone wires can come out of the box, or the box could be closed for use with wireless earphones.

The box could open in any fashion other than by use of a hinge, such as by use of a sliding panel, separable top and bottom, etc.

Instead of a small box, a larger box could be used to sterilize larger earphones. One or more light sources may also be included to provide a directed or more generalize sterilizing field.

Wood, metal, or any combination of different manufacturing materials could be used in addition to, or instead of plastic.

A rechargeable battery system could supplement the need for disposable batteries. The rechargeable battery system could be recharged via a USB cord or solar panels. A power cord that plugs in to a standard electric wall socket could supplement the need for an onboard power supply.

A manual power-on system such as a switch that the user engages could be used instead of an automatic power-on system. The actuated power switch may be a convention on/off switch or button that a user turns the light source on and off. The actuated power switch may also initiate the light source or turn the light source on, but the system may use an automatic shut off such that the light source turns off after a predetermined period of time.

An intelligent chip and sensors of various types could be used to determine if earphones are in the correct location before operation of the unit begins.

What is claimed is:

1. An apparatus for cleaning earphones, comprising:
   a housing having a first housing portion and second housing portion, the housing having an open configuration and a closed configuration;
   a divider in the housing, the housing and divider defining a first compartment and a second compartment within the housing in the closed configuration;
   a germicidal light source in the first compartment;
   a light shield configured to cover the germicidal light source relative to an opening of the housing when the housing is in the open configuration and provide light access through apertures in the light shield at opposing sides of the light shield; and
   support circuitry coupled to the germicidal light source, the support circuitry arranged in the second compartment such that the support circuitry is shielded from light from the germicidal light source by the divider.

2. The apparatus of claim 1, further comprising a first and a second attachment portion, each attachment portion positioned to support an earbud and maintain the earbud in a desired orientation relative to the germicidal light source.

3. The apparatus of claim 2, wherein the first and second attachment portions each comprise a clamp coupled to the divider, the clamp defining two deformable arms to frictionally engage an earbud positioned therebetween.

4. The apparatus of claim 3, wherein the first and second attachment portions are rotatable about an axis perpendicular to the divider to vary an incident angle of light emitted by the germicidal light source onto an attached earbud.

5. The apparatus of claim 4, wherein the germicidal light source is an elongate light source and the first and second attachment portions are on opposing sides of the light source.

6. The apparatus of claim 5, further comprising a timer configured to shut off light from the germicidal light source after a predetermined period of time after the germicidal light source is initially illuminated.

7. The apparatus of claim 6, further comprising a switch within the second compartment and accessible by a projection on the housing attached within the first compartment and extendable through the divider to contact the switch when the housing is in the closed configuration.

8. The apparatus of claim 7, wherein the light shield covering the germicidal light source is positioned on an opposite side of the germicidal light source from the divider.

9. The apparatus of claim 8, further comprising a manual switch on an exterior surface of the housing.

10. The apparatus of claim 9, wherein the housing comprises an aperture in the closed configuration to pass a cord of the earbud during use.

11. The apparatus of claim 2, further comprising a safety switch configured to prevent the germicidal light source from illuminating when the housing is in the open configuration.

* * * * *